US011327066B2

(12) United States Patent
Chatterjee et al.

(10) Patent No.: US 11,327,066 B2
(45) Date of Patent: May 10, 2022

(54) WATER CONTAMINANT MEASUREMENT SYSTEM AND METHODS FOR MEASURING CONCENTRATION LEVELS OF CONTAMINANTS IN WATER

(71) Applicant: Haier US Appliance Solutions, Inc., Wilmington, DE (US)

(72) Inventors: Somak Chatterjee, Hyderabad (IN); Sharath Chandra Prasad, Hyderabad (IN); Allamneni Naga Tejaswini, Hyderabad (IN); Balaji Srinivasan, Hyderabad (IN); Moinuddin Mohd Bilal, Hyderabad (IN); Gregory Sergeevich Chernov, Louisville, KY (US); Andrew Reinhard Krause, Louisville, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 583 days.

(21) Appl. No.: 16/244,192

(22) Filed: Jan. 10, 2019

(65) Prior Publication Data
US 2020/0225204 A1 Jul. 16, 2020

(51) Int. Cl.
*G01N 33/18* (2006.01)
*G01N 27/416* (2006.01)
*G01N 27/07* (2006.01)

(52) U.S. Cl.
CPC ............ *G01N 33/18* (2013.01); *G01N 27/07* (2013.01); *G01N 27/4163* (2013.01); *G01N 27/4166* (2013.01)

(58) Field of Classification Search
CPC ............... G01N 33/18; G01N 27/4163; G01N 27/4166; G01N 27/07; G01N 33/1813
See application file for complete search history.

(56) References Cited

U.S. PATENT DOCUMENTS 3,383,310 A * 5/1968 Heinzgert ............... B01J 49/85
                                                        210/662
5,990,684 A * 11/1999 Merrill .................. G01N 27/10
                                                        324/439

(Continued)

FOREIGN PATENT DOCUMENTS

CN       102135518 B       7/2011
CN       203101324 U       7/2013

OTHER PUBLICATIONS

Godjevargova et al. (T Godjevargova, A Simeonova, A Dimov, Adsorption of heavy metal ions from aqueous solutions by porous polyacrylonitrile beads, J. Applied Polymer Science 83 (2002) 3036-3044) (Year: 2002).*

(Continued)

*Primary Examiner* — Joshua L Allen
(74) *Attorney, Agent, or Firm* — Dority & Manning, P.A.

(57) ABSTRACT

A contaminant measurement system is provided. The system is operable to detect and measure a concentration level of a preselected contaminant, e.g., lead, in water disposed within a chamber of the system. The system includes a detection agent that is operable to interact with the preselected contaminant in the water. The detection agent can be a plurality of polymeric beads or a membrane, for example. The system has a sensing circuit that includes a pair of electrodes spaced from one another and both at least partially disposed in the water. A controller is communicatively coupled with the sensing circuit and is configured to receive one or more electric signals from the sensing circuit. The controller determines a parameter indicative of the concentration level of the preselected contaminant based on the one or more electrical signals. The controller then determines and outputs the concentration level of the preselected contaminant.

18 Claims, 6 Drawing Sheets

(56) References Cited

U.S. PATENT DOCUMENTS

| | | | |
|---|---|---|---|
| 6,699,384 B1 | 3/2004 | Lin et al. | |
| 2005/0276724 A1* | 12/2005 | Bremauer | B01F 35/754251 422/68.1 |
| 2017/0131253 A1* | 5/2017 | Gutierrez Martinez | G01N 33/0009 |

OTHER PUBLICATIONS

Kiani et al. (GR Kiani, H Sheikhloie, N Arsalani, Heavy metal ion removal from aqueous solutions by functionalized polyacrylonitrile, Desalination 269 (2011) 266-270) (Year: 2011).*
Deng et al. (S Deng, R Bai, JP Chen, Aminated Polyacrylonitrile fibers for lead and copper removal, Langmuir 19 (2003) 5058-5064) (Year: 2003).*
Godjevargova et al. (T Godjevargova, A Simeonova, A Dimov, Adsorption of lead and copper on modified polyacrylonitrile beads, J. Applied Polymer Science 79 (2001) 283-288) (Year: 2001).*
Kampalanonwat et al. (P Kampalanonwat, P Supaphol, Preparation and adsorption behavior of aminated electrospun polyacrylonitrile nanofiber mats for heavy metal ion removal, J. Applied Materials and Interfaces 2(12) (2010) 3619-3627) (Year: 2010).*
Jamil et al. (SNAM Jamil, M Khairuddin, R Daik, Preparation of acrylonitrile/acrylamide copolymer beads via a redox method and their adsorption properties after chemical modification, e-Polymers 15(1) (2015) 45-54) (Year: 2015).*
Simeonova et al. (AK Simeonova, TI Godjevargova, AD Dimov, D Dinkov, Copper removal in fixed beds by modified polyacrylonitrile sorbents, J. Environmental Protection and Ecology 3(3) (2002) 750-761) (Year: 2002).*

* cited by examiner

| CALIBRATION MEASUREMENT | CONCENTRATION LEVEL (ppm) | REFERENCE PARAMETER VALUE (mV) | PARAMETER DIFFERENCE VALUE (mV) |
|---|---|---|---|
| BASE MEASUREMENT | 0 | 10 | 0 |
| SECOND MEASUREMENT | 1 | 50 | 40 |
| THIRD MEASUREMENT | 10 | 80 | 70 |
| FOURTH MEASUREMENT | 100 | 150 | 140 |
| FIFTH MEASUREMENT | 1000 | 200 | 190 |

WATER CONTAMINANT MEASUREMENT SYSTEM AND METHODS FOR MEASURING CONCENTRATION LEVELS OF CONTAMINANTS IN WATER

FIELD OF THE INVENTION

The present subject matter relates generally to water quality analysis systems and methods for detecting contaminants in water, such as e.g., lead.

BACKGROUND OF THE INVENTION

Water is an essential element for life and has many uses. Generally, it is desirable to remove contaminants from water designated for safe drinking and use. This may be done via known treatment and filtration processes. In some instances, however, water designated for use may not be properly treated or may contain certain contaminants, such as e.g., lead, cadmium, chromium, and other toxic heavy metals, etc. Such contaminants may be harmful to human health and thus it is desirable to detect such contaminated water and ensure that it is not used. Conventional systems and processes for detecting and measuring concentration levels of contaminants in water have been unsatisfactory. For instance, conventional systems for measuring concentration levels of contaminants in water are relatively expensive and the process for detecting and measuring concentration levels typically has a long turnaround time and must be conducted at an offsite laboratory.

Accordingly, a water contaminant measurement system and methods for detecting and measuring concentration levels of preselected contaminants in water that address one or more of the challenges noted above would be useful.

BRIEF DESCRIPTION OF THE INVENTION

Aspects and advantages of the invention will be set forth in part in the following description, or may be apparent from the description, or may be learned through practice of the invention.

In one exemplary aspect, a contaminant measurement system for measuring a concentration level of a preselected contaminant in a volume of water is provided. The contaminant measurement system includes a housing defining a chamber configured for receipt of the volume of water. Further, the contaminant measurement system includes a detection agent disposed in the volume of water in the chamber, the detection agent configured to selectively interact with the preselected contaminant in the volume of water in the chamber. Further, the contaminant measurement system includes a sensing circuit having a first electrode and a second electrode both disposed at least partially in the volume of water in the chamber, the first electrode spaced at a distance from the second electrode. Moreover, the contaminant measurement system includes a controller in electrical communication with the sensing circuit. The controller is configured to: receive one or more electric signals from the sensing circuit; determine a parameter value indicative of the concentration level of the preselected contaminant in the volume of water based at least in part on the one or more electric signals; determine the concentration level of the preselected contaminant in the volume of water in the chamber based at least in part on the parameter value; and output the concentration level of the preselected contaminant in the volume of water in the chamber.

In another exemplary aspect, a method for measuring a concentration level of a preselected contaminant in a volume of water disposed within a chamber of a contaminant measurement system is provided. The method includes selectively interacting a detecting agent immersed in the volume of water with the preselected contaminant in the volume of water for a first time period. Further, the method includes receiving, from a sensing circuit comprised of a first electrode and a second electrode both at least partially disposed in the volume of water, one or more electric signals. In addition, the method includes determining a parameter value indicative of the concentration level of the preselected contaminant in the volume of water based at least in part on the one or more signals. In addition, the method includes determining the concentration level of the preselected contaminant in the volume of water within the chamber based at least in part on the determined parameter value. Furthermore, the method includes outputting the determined concentration level of the preselected contaminant in the volume of water within the chamber.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
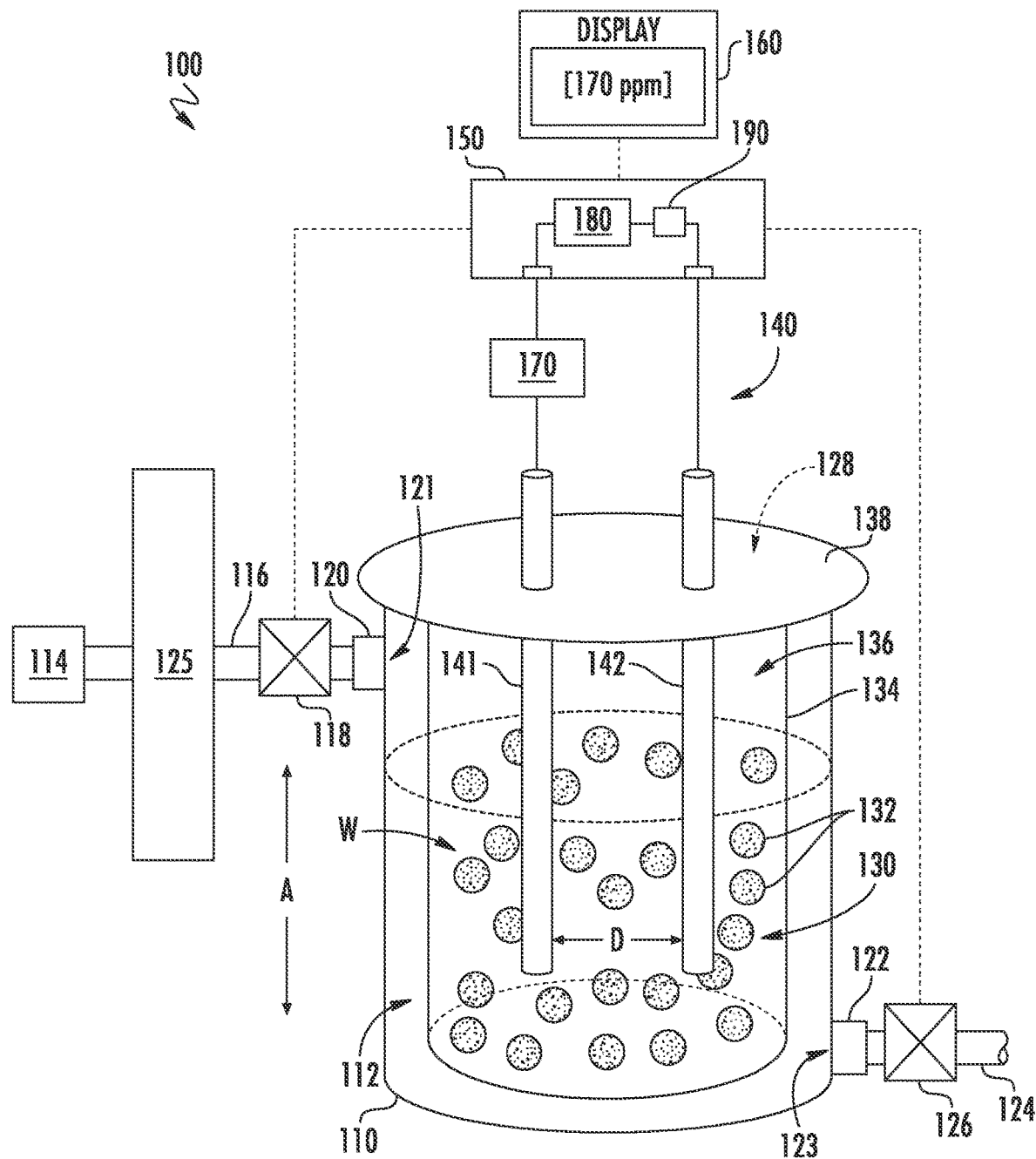
FIG. 1 provides a schematic view of an exemplary water contaminant measurement system according to an exemplary embodiment of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, terms of approximation, such as "approximately," "substantially," or "about," refer to being within a ten percent (10%) margin of error of the stated value. Moreover, as used herein, the terms "first", "second", and "third" may be used interchangeably to distinguish one component from another and are not intended to signify location or importance of the individual components. The terms "upstream" and "downstream" refer to the relative direction with respect to fluid flow in a fluid pathway. For example, "upstream" refers to the direction from which the fluid flows, and "downstream" refers to the direction to which the fluid flows.

FIG. 1 provides a schematic view of an exemplary water contaminant measurement system 100 according to an exemplary embodiment of the present subject matter. Generally, water contaminant measurement system 100 is operatively configured to detect and measure a concentration or concentration level of a preselected contaminant (e.g., lead) in water. The concentration level of output by system 100 may be presented to a user, e.g., so that corrective or preventative action may be taken in the event the concentration level of the preselected contaminant is above a safe drinking or use threshold (e.g., 10 micrograms per liter). Water contaminant measurement system 100 can be located in a number of suitable locations, such as e.g., within a refrigerator appliance as a point of use application, connected to a water supply line of a household or building as a point of entry application, in a water treatment plant, in fluid communication with a well, or in other suitable locations and for other suitable applications. In some embodiments, water contaminant measurement system 100 may be a dynamic system that is operable to detect and measure the concentration level of a preselected contaminant, e.g., lead, in a continuous flow of water. In yet other embodiments, water contaminant measurement system 100 may be a static system that is operable to detect and measure the concentration level of a preselected contaminant in a static volume of water.

As shown in FIG. 1, water contaminant measurement system 100 includes a cylinder or housing 110 defining a chamber 112 configured for receipt of a volume of water W. Housing 110 extends between a top end and a bottom end along an axial direction A. Housing has an inlet port 120 defining an inlet 121 of chamber 112 and an outlet port 122 defining an outlet 123 of chamber 112. Inlet port 120 is positioned at or adjacent the top end of housing 110 and outlet port 122 is positioned at or adjacent the bottom end of housing 110. Inlet port 120 and outlet port 122 may be positioned in other suitable locations as well such that the water can drain off easily.

For this embodiment, chamber 112 is in fluid communication with a water source 114, such as e.g., a water line of a home or water treatment plant. Particularly, an inlet supply conduit 116 provides fluid communication between water source 114 and inlet 121 of chamber 112. An inlet valve 118 is positioned along inlet supply conduit 116 and is operable to selectively allow a volume of water to flow into chamber 112 through inlet 121 of chamber 112. Inlet valve 118 is movable between an open position in which fluid may flow through inlet valve 118 and a closed position in which fluid is prevented from flowing through inlet valve 118. Water W may drain from chamber 112 through outlet 123 via an outlet supply conduit 124 in fluid communication with outlet 123. Outlet supply conduit 124 is operable to allow water to drain from chamber 112. An outlet valve 126 is positioned along outlet supply conduit 124 to selectively allow the volume of water W within chamber 112 to drain therefrom. Outlet valve 126 is movable between an open position in which fluid may flow through outlet valve 126 and a closed position in which fluid is prevented from flowing through outlet valve 126. Inlet valve 118 and outlet valve 126 may both be normally closed solenoid valves, for example, and may both be communicatively coupled with a controller of water contaminant measurement system 100 so that they may be controlled to move between their respective open and closed positions.

In some alternative embodiments, chamber 112 may not include inlet and outlet ports, inlet and outlet conduits, or inlet and outlet valves. Rather, in such embodiments, chamber 112 has an opening 128 at a top end of housing 110 that provides selective access to chamber 112, e.g., for pouring into or removing water from chamber 112. Accordingly, in such embodiments, water contaminant measurement system 100 can be a static or standalone system, which can be used to access the water quality directly at an affected site, e.g., river, ponds, lakes. Thus, notably, in some embodiments, water measurement system 100 is mobile or capable of easily being transported from one location to another.

Water contaminant measurement system 100 includes a detection agent 130 disposed in the volume of water W within chamber 112. Detection agent 130 is operatively configured to selectively interact with a preselected contaminant in the water W within chamber 112. Without wishing to be bound by any particular theory, the interaction between ions of the preselected contaminant and detection agent 130 may be ionic bonding, electrostatic attraction (e.g., hydrogen bonding), van der Waals forces, etc., which changes the conductivity/resistivity of the water mixture. Detection agent 130 may be any suitable type of medium or membrane capable of selectively interacting with a designated or preselected contaminant in the water W. By way of example, the contaminant or pollutant may be lead, another heavy metal, some non-metal contaminant, chlorine, chloroform, cadmium, chromium, phenols, pharmaceuticals, microbes, cysts, arsenic, and/or other undesirable substances or compounds.

The chemistry of detection agent 130 is preferably selected such that detection agent 130 selectively interacts with a contaminant that is desired to be measured. For instance, for this embodiment, detection agent 130 is a plurality of polymeric beads 132. More specifically, the plurality of beads 132 are sodium hydroxide treated polyacrylonitrile homopolymer beads. The plurality of beads 132 depicted in FIG. 1 have been surface treated and formed with materials such that they are configured to interact with lead ions within the volume of water W in chamber 112. For example, the nitrile groups of the polyacrylonitrile homopolymer beads 132 may interact with the lead ions (e.g., via ionic bonding, electrostatic attraction (e.g., hydrogen bonding), van der Waals forces, etc.), e.g., to change the conductivity/resistivity of the water mixture or the voltage across or current flowing between opposing electrodes. In some embodiments, the synthesized beads 132 may be prepared by dissolution of a polymer (e.g., polyacrylonitrile homopolymer) in a solvent (dimethyl-form-amide) and extrusion through a needle assembly followed by transformation of the liquid solution to a gel capsular structure. Afterwards, the beads 132 may be treated with sodium hydroxide, having a strength varying from 0.1(N) to 1(N) for about twenty-four (24) hours. Although the beads 132 are shown as having spherical shapes, these interacting agents 132 may have other suitable shapes.

As further depicted in FIG. 1, the plurality of beads 132 or detection agent 130 may be housed or contained within a basket chamber 136 defined by a basket 134. Basket 134 has a plurality of perforations (not shown) that provide fluid communication between chamber 112 and basket chamber 136 of basket 134. Basket 134 is removably insertable into chamber 112 of housing 110. When basket 134 is inserted into chamber 112, a top cap 138 engages a rim of the housing and is seated thereon. Top cap 138 has a greater diameter than the diameter of opening 128 so that a user may easily grasp top cap 138 and remove basket 134 from chamber 112. As depicted in FIG. 1, top cap 138 is configured to hold and secure a pair of opposing electrodes of the system in place. Accordingly, the entire electrochemical cell and basket may easily be inserted into or removed from chamber 112 of housing 110.

Water contaminant measurement system 100 includes a sensing circuit 140 for detecting and measuring a contaminant concentration level of a preselected containment in the volume of water W in chamber 112. The sensing circuit 140 includes a first electrode 141 disposed at least partially in the volume of water W in chamber 112. Sensing circuit 140 also includes a second electrode 142 spaced from first electrode 141, e.g., by a distance D. Like first electrode 141, second electrode 142 is disposed at least partially in the volume of water W in chamber 112 of housing 110. First electrode 141 may be a cathode and second electrode 142 may be an anode, or vice versa. First electrode 141 and second electrode 142 may be spaced from one another by any suitable distance. As one example, the distance D between first electrode 141 and second electrode 142 may be about one millimeter (1 mm). Top cap 138 may retain and keep proper spacing between first electrode 141 and second electrode 142.

First electrode 141 and second electrode 142 are formed of dissimilar conducting materials. For this embodiment, first electrode 141 is formed of a first electrically conducting material and second electrode 142 is formed of a second electrically conducting material that is dissimilar to the first electrically conducting material of first electrode 141. As one example, the first electrically conducting material of first electrode 141 may be copper and the second electrically conducting material of second electrode 142 may be graphite. However, the electrodes 141, 142 may be formed of other materials as well, such as e.g., platinum, gold, or other carbon materials. Preferably, at least one of first electrode 141 and second electrode 142 is inert and the other electrode is reactive. In some embodiments, first electrode 141 or second electrode 142 is coated with a suitable material.

A controller 150 is in electrical communication with sensing circuit 140, e.g., via one or more wired or wireless communication links. Generally, operation of water contaminant measurement system 100 is controlled by controller 150. Further, controller 150 is configured to output a concentration level of a preselected contaminant in the volume of water W in chamber 112 as will be described in detail herein. Controller 150 may be communicatively coupled with a control panel (not shown) so that a user may control and set features of system 100. The control panel may be a control panel dedicated to system 100 or may be a multiuse control panel, such as e.g., a control panel for a refrigerator appliance. In response to user manipulation of one or more user controls of the control panel, controller 150 performs one or more operations. As described in more detail below with respect to FIG. 2, controller 150 may include a memory and microprocessor, such as a general or special purpose microprocessor operable to execute programming instructions or micro-control code associated with methods described herein. Alternatively, controller 150 may be constructed without using a microprocessor, e.g., using a combination of discrete analog and/or digital logic circuitry (such as switches, amplifiers, integrators, comparators, flip-flops, AND gates, and the like) to perform control functionality instead of relying upon software.

The control panel and other components of system 100 may be in communication with controller 150 via one or more signal lines or shared communication busses. For instance, as shown in FIG. 1, controller 150 is communicatively coupled with inlet valve 118 and outlet valve 126. Further, controller 150 is communicatively coupled with a display device 160. As will be described below, in some embodiments, the contaminant concentration level is output by controller 150 to display device 160 so that the determined contaminant concentration level is presented to a user. For instance, as shown in FIG. 1, display device 160 may present a particular concentration level (e.g., "170 ppm") to a user as parts per million (ppm) or in some other suitable units. Display device 160 may be any suitable display. For instance, display device 160 may be an LCD, LED, or OLED display. In some embodiments, display device 160 and controller 150 are both positioned onboard the same control board. In other embodiments, display device 160 may be a display of an appliance (e.g., a refrigerator appliance) or other device to which water contaminant measurement system 100 is connected.

Figure 2:
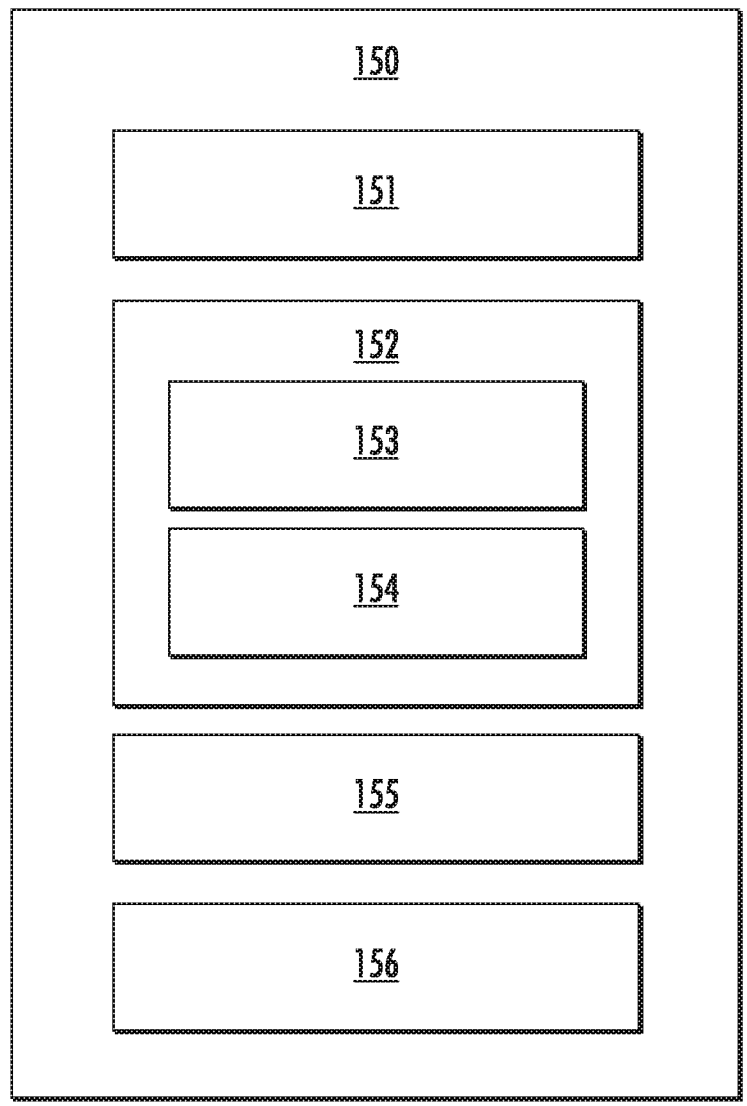
FIG. 2 provides a schematic view of a controller of the water contaminant measurement system of FIG. 1 according to example embodiments of the present subject matter.

FIG. 2 provides a schematic view of controller 150 of water contaminant measurement system 100 of FIG. 1 according to example embodiments of the present disclosure. Controller 150 may be used to implement water contaminant measurement system 100 and methods described herein. Although shown as a single device, it will be appreciated that water contaminant measurement system 100 can include one or more controllers. As shown, controller 150 can include one or more processor(s) 151 and one or more memory device(s) 152. The one or more processor(s) 151 can include any suitable processing device, such as a microprocessor, microcontroller, integrated circuit, an application specific integrated circuit (ASIC), a digital signal processor (DSP), a field-programmable gate array (FPGA), logic device, one or more central processing units (CPUs), graphics processing units (GPUs) (e.g., dedicated to efficiently rendering images), processing units performing other specialized calculations, etc. The memory device(s) 152 can include one or more non-transitory computer-readable storage medium(s), such as RAM, ROM, EEPROM, EPROM, flash memory devices, magnetic disks, etc., and/or combinations thereof.

The memory device(s) 152 can include one or more computer-readable media and can store information accessible by the one or more processor(s) 151, including instructions 153 that can be executed by the one or more processor(s) 151. For instance, the memory device(s) 152 can store instructions 153 for running one or more software applications, displaying a user interface, receiving user input, processing user input, etc. In some implementations, the instructions 153 can be executed by the one or more processor(s) 151 to cause the one or more processor(s) 151 to perform operations, e.g., such as one or more portions of methods described herein. The instructions 153 can be software written in any suitable programming language or can be implemented in hardware. Additionally, and/or alternatively, the instructions 153 can be executed in logically and/or virtually separate threads on processor(s) 151.

The one or more memory device(s) 152 can also store data 154 that can be retrieved, manipulated, created, or stored by the one or more processor(s) 151. The data 154 can include, for instance, data to facilitate performance of methods described herein. The data 154 can be stored in one or more database(s). The one or more database(s) can be connected to controller 150 by a high bandwidth LAN or WAN, or can also be connected to controller 150 through network(s) (not shown). The one or more database(s) can be split up so that they are located in multiple locales. In some implementations, the data 154 can be received from another device.

Controller 150 can also include a communication module or interface 155 used to communicate with one or more other component(s) of controller 150 over the network(s). The communication interface 155 can include any suitable components for interfacing with one or more network(s), including for example, transmitters, receivers, ports, controllers, antennas, or other suitable components. Further, controller 150 can include a machine-learned model 156 that is operable to adjust a parameter trend line as will be described herein.

With reference again to FIG. 1, in some exemplary embodiments, water contaminant measurement system 100 can optionally include a power supply 170 positioned along sensing circuit 140. Power supply 170 may be any suitable device capable of flowing an electric current through sensing circuit 140. By way of example, power supply 170 may be, e.g., a battery, a DC power supply, an AC power supply, an AC actuator, etc. In some embodiments, power supply 170 is operable to apply a voltage to the electrodes 141, 142, e.g., to better maintain the polarities of the electrodes 141, 142.

In yet other embodiments, water contaminant measurement system 100 can optionally include a measurement device 180. Measurement device 180 is positioned along and in electrical communication with sensing circuit 140. For this embodiment, measurement device 180 is positioned on the same control board as controller 150; however, in other embodiments, measurement device 180 may be positioned offboard the control board of controller 150. Measurement device 180 is operable to determine a parameter value based on one or more electric signals received from electrodes 141, 142. By way of example, measurement device 180 may be a multimeter, a voltmeter, an ampimeter, an electrical conductivity meter (EC), or some other device operable for converting or determining a parameter based on one or more electrical signals received. Example parameters include a voltage between first electrode 141 and second electrode 142, an electrolytic current flowing between first electrode 141 and second electrode 142 (and thus through sensing circuit 140), a conductivity of the volume of the water W within chamber 112, and a resistivity of the volume of water W within chamber 112. As noted above, water contaminant measurement system 100 can optionally include measurement device 180. In some alternative exemplary embodiments, controller 150 may include an analog reading chip, a software program or application, or a combination thereof that is operable to interpret incoming electrical signals and determine or convert the electrical signals into a parameter value, e.g., a voltage, a current, an electrical conductance, or a resistivity.

In some other embodiments, water contaminant measurement system 100 can optionally include an amplification circuit 190 positioned along and in electrical communication with sensing circuit 140. Amplification circuit 190 is operable to amplify electric signals received from electrodes 141, 142. The amplified signals may then be routed to a filter, measurement device 180, or to processor(s) 151 of controller 150 for processing. Amplification circuit 190 can include electrical components for amplifying an electrical signal, such as e.g., diodes, capacitors, resistors, etc.

In some embodiments, a filter device is optionally positioned upstream and/or downstream of chamber 112 of water contaminant measurement system 100. For this embodiment, a filter device 125 is positioned along inlet supply conduit 116 upstream of chamber 112. Filter device 125 is operable to remove certain contaminants from the water flowing from water source 114 through water contaminant measurement system 100 and to a downstream destination. Particularly, filter device 125 can be operable to filter suspended solids, total dissolved solids, and/or large size particulates (e.g., sand particles) from the water stream. Advantageously, removal of such solids and large size particulates may provide for more accurate concentration level measurements and may prevent the detecting agent 130 or beads 132 from being damaged. In some embodiments, chamber 112 of housing 110 may be integrated into filtration device 125 such that filter device 125 and water contaminant measurement system 100 are configured as a single unit.

General operation of water contaminant measurement system 100 will now be described. After calibrating water contaminant measurement system 100, and more particularly controller 150 (e.g., in a manner described in detail below), water contaminant measurement system 100 is operatively configured to detect and measure a concentration level of a preselected contaminant in a volume of water W. The volume of water W is provided to chamber 112 of housing 110. When the volume of water W enters chamber 112, detecting agent 130 becomes immersed in the water W. In this embodiment, detecting agent 130 is polymeric beads 132 that are configured to interact with ions of the preselected contaminant (e.g., lead). When the lead ions interact with the polymeric beads 132, the conductivity/resistivity of the water mixture changes. Sensing circuit 140, via electrodes 141, 142, senses this change and one or more signals are received by measurement device 180 and/or controller 150. The sensed signals are converted into a parameter value, such as e.g., a voltage, a current, an electrical conductance, or a resistivity. That is, controller 150 or measurement device 180 determines a parameter value based on the one or more signals. Controller 150 receives the determined parameter value (e.g., a voltage) and determines the concentration level of the preselected contaminant based on the determined parameter value. The parameter value used to determine the concentration level may be a predicted value or may be a measured value. The determined concentration level may then be output. For instance, the concentration level may be output to display device 160 such that the concentration level may be presented to a user, e.g., as shown in FIG. 1. An exemplary manner in which water contaminant measurement system 100 may determine a concentration level of a preselected contaminant is provided in greater detail below.

Figure 3:
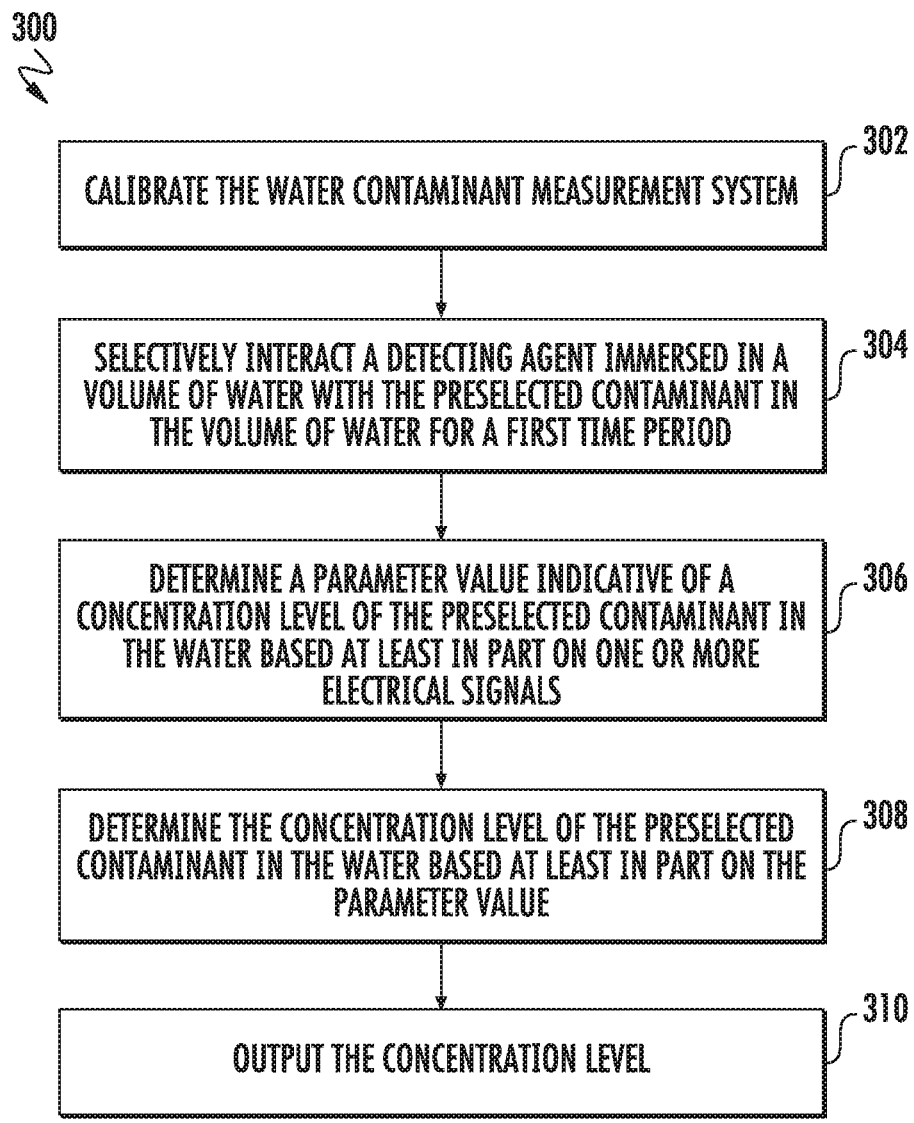
FIG. 3 provides a flow diagram of an exemplary method for detecting and measuring a concentration level of a preselected contaminant in a volume of water according to an exemplary embodiment of the present subject matter.

FIG. 3 provides a flow diagram of an exemplary method (300) for detecting and measuring a concentration level of a preselected contaminant in a volume of water according to an exemplary embodiment of the present subject matter. For instance, various components of the water contaminant measurement system 100 of FIG. 1 may detect and measure a concentration level of a preselected contaminant in a volume of water in accordance with method (300). Accordingly, general reference is made to FIG. 1 and the reference numerals used to denote the features of water contaminant measurement system 100 will be utilized for context below.

At (302), the method (300) includes calibrating the system, and more particularly, calibrating a controller of the contaminant measurement system. An example manner in which the controller may be calibrated at (302) is provided below with reference to method (400) as depicted in FIG. 4.

Figure 4:
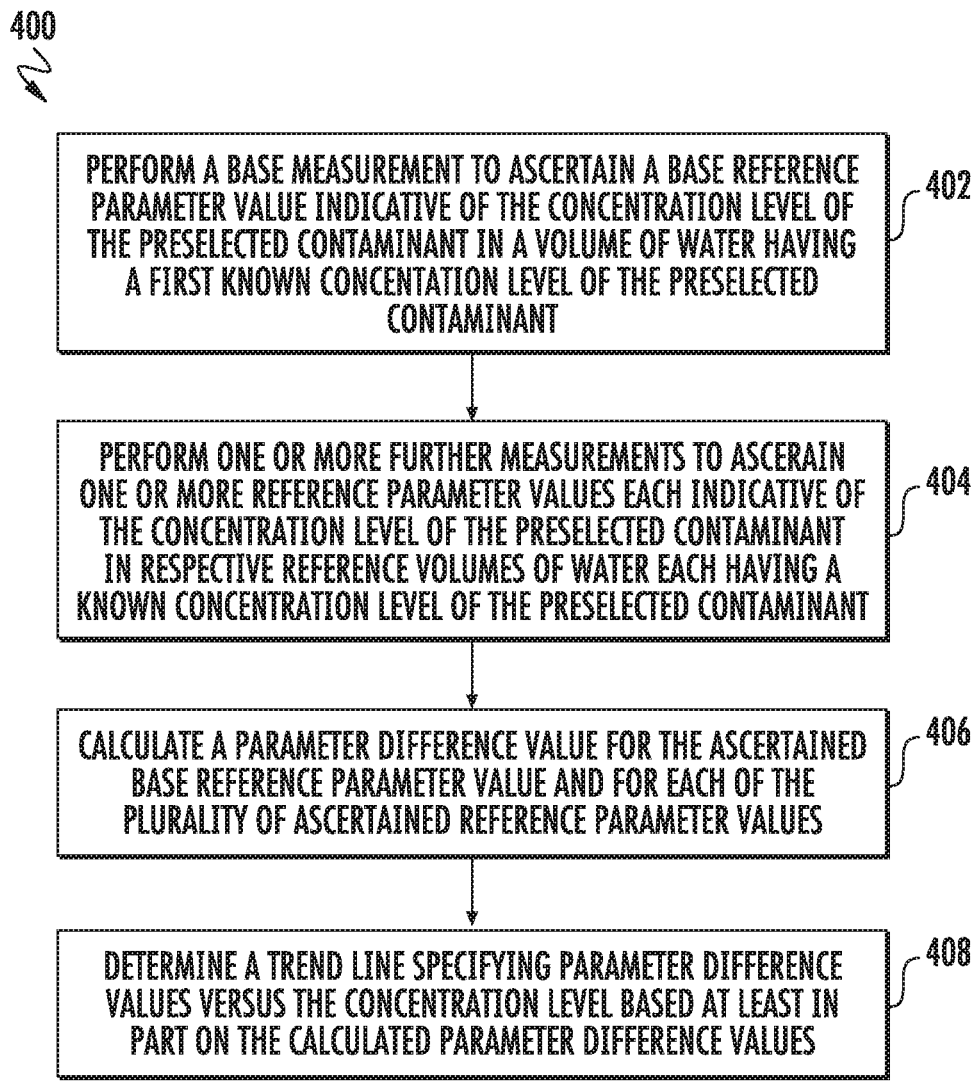
FIG. 4 provides a flow diagram of an exemplary method for calibrating the water contaminant measurement system according to an exemplary embodiment of the present subject matter.
Figures 5, 6:
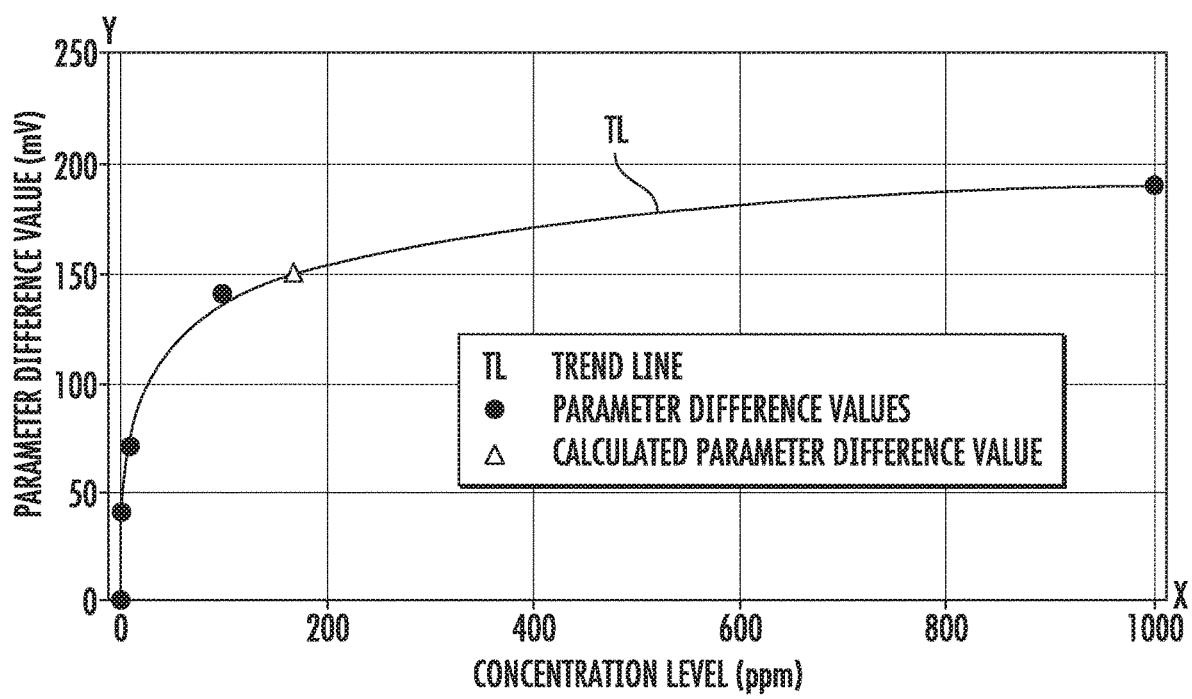
FIG. 5 provides a graph depicting an example manner in which the method of FIG. 4 may be implemented according to an exemplary embodiment of the present subject matter.
FIG. 6 provides a table corresponding to the graph of FIG. 5.

With reference now to FIGS. 4, 5, and 6, FIG. 4 provides a flow diagram of one exemplary method (400) in which a controller of a water contaminant measurement system may be calibrated at (302) of the method (300) of FIG. 3 according to an exemplary embodiment of the present subject matter. FIG. 5 provides an exemplary graph illustrating an example implementation of method (400) according to an exemplary embodiment of the present subject matter. FIG. 6 provides a table corresponding to the graph of FIG. 5.

At (402), the method (400) for calibrating the controller includes performing a base measurement to ascertain a base reference parameter value indicative of the concentration level of the preselected contaminant in a volume of water having a first known concentration level of the preselected contaminant.

For instance, as shown in the example of FIGS. 5 and 6, the first known concentration level of the preselected contaminant in the volume of water was selected as zero (0) ppm. Hence, the volume of water having the first known concentration level of the preselected contaminant had zero (0) ppm or a negligible amount of the preselected contaminant. To ascertain the base reference parameter, the volume of water having the first known concentration level was provided into chamber 112 of housing 110. Detection agent 130 attempted to interact with the preselected contaminant from the volume of water having the first known concentration. As the volume of water having the first known concentration did not contain (or had a negligible amount of) the preselected contaminant, detection agent 130 did not interact with any ions of the preselected contaminant (or a negligible amount). One or more electric signals were received by controller 150 from sensing circuit 140. The one or more electric signals were representative of the base reference parameter value indicative of the concentration level of the preselected contaminant in the volume of water having the first known solution. Controller 150 determined the base reference parameter value, e.g., via an analog reading chip. For the example of FIGS. 5 and 6, the measured parameter is the voltage between first electrode 141 and second electrode 142 and the base reference parameter value was determined to be ten millivolts (10 mV) as shown in the table in FIG. 6. Accordingly, the voltage between first electrode 141 and second electrode 142 was ten millivolts (10 mV) for the volume of water having a concentration level of zero (0) ppm or a negligible amount of the preselected contaminant.

At (404), the method (400) for calibrating the controller includes performing one or more further measurements to ascertain one or more reference parameter values each indicative of the concentration level of the preselected contaminant in respective reference volumes of water each having a known concentration level of the preselected contaminant.

For the example of FIGS. 5 and 6, a second measurement was performed to ascertain a second reference parameter value associated with a second volume of water having a second known concentration level of the preselected contaminant, a third measurement was performed to ascertain a third reference parameter value associated with a third volume of water having a third known concentration level of the preselected contaminant, a fourth measurement was performed to ascertain a fourth reference parameter value associated with a fourth volume of water having a fourth known concentration level of the preselected contaminant, and a fifth measurement was performed to ascertain a fifth reference parameter value associated with a fifth volume of water having a fifth known concentration level of the preselected contaminant.

The second measurement was performed to ascertain the second reference parameter value for the second volume of water having a second known concentration. To ascertain the second reference parameter value, the second volume of water having the second known concentration level was provided into chamber 112 of housing 110 (the first volume of water having the first known concentration level was first drained). Detection agent 130 interacted the preselected contaminant from the second volume of water having the second known concentration. The interaction between the detection agent 130 and the ions of the preselected contaminant as well as the reactions at the first and second electrodes 141, 142 causes the reference parameter value (e.g., the voltage) to increase. One or more electric signals were received by controller 150 from sensing circuit 140 and controller 150 determined a second reference parameter value. For the example of FIGS. 5 and 6, the measured parameter was selected as the voltage (e.g., the potential difference) between first electrode 141 and second electrode 142 and the second reference parameter value was determined to be fifty millivolts (50 mV). Thus, for this example, the voltage between first electrode 141 and second electrode 142 was determined to be fifty millivolts (50 mV) for a volume of water having a concentration level of one (1) ppm of the preselected contaminant. Notably, controller 150 determined the second reference parameter value at a time in which the measured voltage reached steady state. The measured voltage or parameter may fluctuate for a time period after the ions of the preselected contaminant within the second volume of water and detection agent 130 interact. Accordingly, the reference parameters are determined by controller 150 after equilibrium is achieved within chamber 112 and the reference parameter reaches steady state.

The same process was followed for the other reference parameters. For this example, the third known concentration level of the preselected contaminant in the third volume of water was ten (10) ppm and the third reference parameter value was measured at eighty millivolts (80 mV). The fourth known concentration level of the preselected contaminant in the fourth volume of water was one hundred (100) ppm and the fourth reference parameter value was measured at one hundred fifty millivolts (150 mV). The fifth known concentration level of the preselected contaminant in the fifth volume of water was one thousand (1,000) ppm and the fifth reference parameter value was measured at two hundred millivolts (200 mV). Although a total of five (5) measurements were performed in this example, it will be appreciated that more or less than five (5) measurements may be performed during calibration.

At (406), the method (400) for calibrating the controller further includes calculating a parameter difference value for the ascertained base reference parameter value and each of the plurality of ascertained reference parameter values. The parameter difference value for each of the plurality of ascertained reference parameter values is descriptive of the ascertained base reference parameter value subtracted from a given one of the ascertained reference parameter value. The parameter difference value for the base reference parameter value is zero (0), or the base reference parameter subtracted from the base reference parameter.

Continuing with the example of FIGS. 5 and 6, the parameter difference value associated with the base parameter value (10 mV) was determined to be zero millivolts (0 mV). That is, the base reference parameter was subtracted from the base reference parameter (10 mV−10 mV=0 mV). The parameter difference value associated with the second parameter value (50 mV) was determined to be forty millivolts (40 mV). That is, the base reference parameter was subtracted from the second reference parameter (50 mV−10 mV=40 mV). The parameter difference value associated with the third parameter value (80 mV) was determined to be seventy millivolts (70 mV). That is, the base reference parameter was subtracted from the third reference parameter (80 mV−10 mV=70 mV). The parameter difference value associated with the fourth parameter value (150 mV) was determined to be one hundred forty millivolts (140 mV). That is, the base reference parameter was subtracted from the fourth reference parameter (150 mV−10 mV=140 mV). Finally, the parameter difference value associated with the fifth parameter value (200 mV) was determined to be one hundred ninety millivolts (190 mV). That is, the base reference parameter was subtracted from the fifth reference parameter (200 mV−10 mV=190 mV).

At (408), the method (400) for calibrating the controller includes determining a trend line specifying parameter difference values versus the concentration level based at least in part on the calculated parameter difference values. As shown in the graph of FIG. 5, the calculated parameter difference values may be plotted on a graph as a function of concentration level and a trend line may be fit to the data points. In some implementations, the trend line may be a best-fit trend line. As will be explained in detail herein, the trend line may be utilized to calculate the concentration level of the preselected contaminant in a volume of water having an unknown concentration level.

Returning now to FIG. 3, once the system is calibrated at (302), e.g., via method (400), water contaminant measurement system 100 is now configured and operable to detect and measure the concentration level of a preselected contaminant in a volume of water having an unknown concentration level. Each water contaminant measurement system 100 may be calibrated as described above at (302), e.g., method (400), or in some implementations, other water contaminant measurement systems may be programmed or imaged with the trendline and values noted above. Thus, each water contaminant measurement system need not undergo calibration as described in method (400).

At (304), the method (300) includes selectively interacting a detecting agent immersed in a volume of water with the preselected contaminant in the volume of water for a first time period. For instance, the volume of water may have an unknown concentration level of the preselected contaminant. As one example, with reference to FIG. 1, a volume of water having an unknown concentration level of the preselected contaminant may be provided into chamber 112 of housing 110. For instance, controller 150 may activate inlet valve 118 to move to an open position so that the water may flow from water source 114 to chamber 112 via inlet supply conduit 116. When a predetermined volume of water having an unknown concentration level of the preselected contaminant has filled into chamber 112, controller 150 may control inlet valve 118 to move to a closed position to prevent more water from flowing into chamber 112. When the volume of water having an unknown concentration level of the preselected contaminant fills into chamber 112, detecting agent 130 becomes immersed in the volume of water W and interacts with the preselected contaminant in the volume of water for a first time period. Of course, if the volume of water having the unknown concentration level of the preselected contaminant does not in fact contain the preselected contaminant, detecting agent 130 will not interact with the preselected contaminant.

In some implementations, the preselected contaminant is lead. In such implementations, detecting agent 130 is selected as polymeric beads 132 that are specifically designed to detect and w lead. The plurality of beads 132 may be treated with sodium hydroxide and may be polyacrylonitrile homopolymer beads. In some alternative implementations, the preselected contaminant may be another heavy metal, such as e.g., cadmium or chromium. In such implementations, the detecting agent 130, which may be beads 132, may be treated with other solutions and may have a different chemistry than the polymeric beads 132 specifically designed to interact with lead. In some further implementations, the contaminant may be phenols, pharmaceuticals, microbes, cysts, arsenic, and/or other undesirable substances or compounds.

At (306), the method (300) includes receiving, from a sensing circuit comprised of a first electrode and a second electrode both at least partially disposed in the volume of water, one or more electric signals. For instance, during or at the end of the first time period, controller 150 or measurement device 180 may receive the one or more electric signals from sensing circuit 140 that includes first and second electrodes 141, 142 disposed within the volume of water in chamber 112. The one or more electric signals are representative of a parameter indicative of the concentration level of the preselected contaminant in the volume of water W. For instance, the parameter may be a voltage, a current, an electrical conductance, or a resistivity. As noted previously, as detecting agent 130 interacts with the preselected contaminant (e.g., lead), the voltage across and the current flowing between the first and second electrodes 141, 142 change. This also causes a change in the electrical conductivity of the water, or inversely, its resistivity. Thus, such electrical signals may be indicative of any one of these parameters. Based at least in part on the electric signals, e.g., the amplitude of the signals, a parameter value may be determined as discussed below at (308).

The one or more electric signals may be received by controller 150 or measurement device 180 at (306) continuously throughout the first time period, at a predetermined interval throughout the first time period (e.g., every five seconds), or only at the end of the first time period. The first time period may extend from a start time to an end time. In some implementations, the parameter value used to determine the concentration level of the contaminant in the volume of water within the chamber at (310) is based on one or more final signals of the one or more signals received at an end time of the first time period.

At (308), the method (300) includes determining a parameter value indicative of the concentration level of the preselected contaminant in the volume of water based at least in part on the one or more signals. For instance, upon receiving the one or more electric signals, controller 150 or measurement device 180 may determine or convert the one or more electric signals into a parameter value. For example, supposing the designated parameter is voltage, controller 150 may determine the voltage across first electrode 141 and second electrode 142 by converting the one or more electric signals into the voltage. As another example, supposing the designated parameter is current, controller 150 may determine the electrolytic current flowing between first electrode 141 and second electrode 142 by converting the one or more electric signals into the electric current. In some implementations, the parameter value is indicative of at least one of a voltage between the first electrode and the second electrode, an electrolytic current flowing between the first electrode and the second electrode, a conductivity of the volume of the water within the chamber, and a resistivity of the volume of water within the chamber.

Moreover, in some implementations, the end time of the first time period is associated with the determined parameter obtaining or reaching a steady state. Thus, in such implementations, the end time of the first time period is determined based on the determined parameter value reaching a steady state. For example, supposing the parameter is voltage, if the determined voltage maintains a value within a predetermined range for a predetermined time, controller 150 determines that the parameter has reached a steady state. Then, at (308), controller 150 may determine the parameter value based on the one or more final signals of the one or more signals received at an end time of the first time period.

At (310), the method (300) includes determining the concentration level of the preselected contaminant in the volume of water within the chamber based at least in part on the determined parameter value. For instance, the concentration level of the preselected contaminant in the volume of water W within chamber 112 may be determined based at least in part on the parameter value determined at (308). In some implementations, determining the concentration level of the preselected contaminant in the volume of water within the chamber based at least in part on the determined parameter value includes: calculating a parameter difference value for the determined parameter, wherein the parameter difference value for the determined parameter is descriptive of the ascertained base reference parameter value subtracted from the determined parameter value; and correlating the calculated parameter difference value for the determined parameter to the concentration level of the preselected contaminant in the volume of water within the chamber utilizing the determined trend line.

By way of example, with reference again to FIG. 5, suppose the parameter value determined at (308) is a voltage of one hundred sixty millivolts (160 mV). To determine the concentration level of the preselected contaminant (e.g., lead) in the volume of water W within chamber 112 based at least in part on the determined parameter value, a parameter difference value for the determined parameter value (one hundred sixty millivolts (160 mV)) is calculated. The parameter difference value for the determined parameter value is calculated in a similar fashion as the reference parameter values were calculated at (302) of method (300). In particular, the parameter difference value for the determined parameter value is descriptive of the ascertained base reference parameter value (e.g., as ascertained at (402) of method (400)) subtracted from the determined parameter value (e.g., as determined at (308) of method (300)). Thus, in this example, the parameter difference value for the determined parameter value is one hundred fifty millivolts (150 mV) as calculated by (160 mV-10 mV=150 mV).

Thereafter, the calculated parameter difference value (150 mV) for the determined parameter value is correlated to the concentration level of the preselected contaminant in the volume of water within the chamber utilizing the determined trend line. As shown in FIG. 5, the intersection of the calculated parameter difference value (150 mV) and the trend line TL determines the concentration level. The intersection of the calculated parameter difference value (150 mV) and the trend line TL is shown plotted on the graph in FIG. 5, and as depicted, the calculated parameter difference value (150 mV) correlates to a concentration level of about one hundred seventy (170) ppm. Accordingly, the volume of water W disposed in chamber 112 has concentration level of about one hundred seventy (170) ppm of the preselected contaminant (e.g., lead).

At (312), the method (300) includes outputting the determined concentration level of the preselected contaminant in the volume of water in the chamber. For instance, controller 150 may output the concentration level of the preselected contaminant in the volume of water W in chamber 112 as determined at (310) to display device 160. In this way, the determined concentration level is presented to a user. For instance, for the example above, display device 160 may present the concentration level as one hundred seventy (170) ppm.

Further, in some exemplary implementations, method (300) includes applying a voltage across the first electrode and the second electrode both at least partially disposed in the volume of water within the chamber. For instance, power supply 170 may be positioned along sensing circuit 140 and may be configured to apply a voltage to the electrodes 141, 142, e.g., to better maintain the polarities of the electrodes 141, 142. In such implementations, the applied voltage must be taken into account when determining the concentration level of the preselected contaminant.

In some implementations, water contaminant measurement system 100 is configured to rapidly detect and measure a concentration level of a preselected contaminant in a volume of water. In short, in such implementations, one or more electric signals are received during the first time period (e.g., the time period in which detecting agent 130 interacts with the preselected contaminant), and as the signals are received, parameter values are determined and stored as data points. Based on the data points, controller 150 generates a parameter trend line specifying the determined parameter values over time. The parameter trend line is then used to predict a predicted parameter value in which the parameter will reach a steady state. In such implementations, the predicted parameter value is used to determine the concentration level of the contaminant in the volume of water within the chamber at (310).

Figure 7:
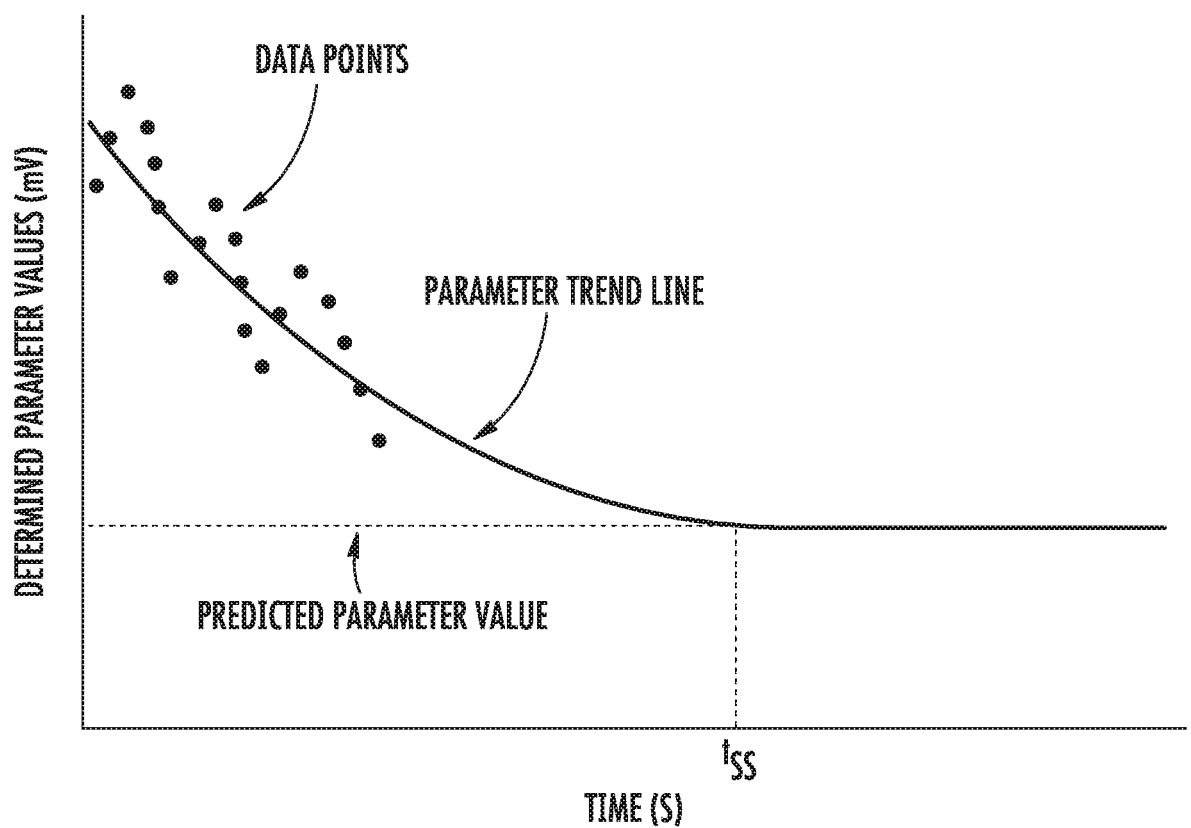
FIG. 7 provides a graph depicting determined parameter values as a function of time according to an exemplary embodiment of the present subject matter.

By way of example, with reference now to FIG. 7, FIG. 7 provides a graph depicting determined parameter values as a function of time. As depicted, in such implementations, the method (300) includes storing a plurality of data points representative of the determined parameter values over the first time period and plotting them as a function of time. The method (300) also includes generating a parameter trend line based at least in part on the stored and plotted plurality of data points. The parameter trend line may be calculated as a linear trend line, an exponential function, a polynomial function, a moving average, etc. In FIG. 6, the parameter trend line is generated as a decaying exponential function. In addition, the method (300) includes predicting the parameter value based at least in part on the parameter trend line. For the example depicted in FIG. 7, controller 150 predicts the parameter value as a value in which the parameter is predicted to reach a steady state, or stated differently, as a value in which the parameter trend line reaches a steady state. In this example, the parameter trend line is predicted to reach a steady state at a time $t=t_{SS}$. The parameter value of the trend line at time $t=t_{SS}$ is determined as the predicted parameter value. In such implementations, the parameter value used to determine the concentration level of the contaminant in the volume of water within the chamber at (310) is based on the predicted parameter value. Advantageously, by predicting the parameter value at steady state, concentration level measurements may be output by controller 150 rapidly, e.g., within seconds, within thirty seconds, within minutes, etc. Thus, consumers may be made aware of potentially unsafe water more rapidly without need to wait hours or days with conventional systems.

In some implementations, controller 150 can include machine-learned model 156 (FIG. 2) that can be used to adjust the parameter trend line to more accurately predict the parameter value at steady state. In such embodiments, for example, the machine-learned model 156 can be adjusted based at least in part on validated parameter values. That is, the machine-learned model may adjust the parameter trend line based on the correlation between the predicted parameter values and the actual parameter values measured when the parameter has in fact reached steady state. The machine-learned model may also be trained and adjusted based on a plurality on measurement variables, such as e.g., the number of measurements performed by water contaminant measurement system 100, the time in service of water contaminant measurement system 100, the materials used for the electrodes, the spacing between the electrodes (i.e., the distance D), the water source, the number and type of detecting agents (e.g., the number of beads), the method in which the detecting agents are formed, the preselected contaminant, the volume of water used for sampling or determining the concentration level of the preselected contaminant, the measurement device or software program logic used for the measurements, whether a power source is utilized, and if so, the type of power rating the of power supply, etc.

The machine-learned model 156 can use any suitable machine learning technique to adjust the parameter trend line. For example, machine-learned model 156 can include a machine or statistical learning model structured as one of a linear discriminant analysis model, a partial least squares discriminant analysis model, a support vector machine model, a random tree model, a logistic regression model, a naïve Bayes model, a K-nearest neighbor model, a quadratic discriminant analysis model, an anomaly detection model, a boosted and bagged decision tree model, an artificial neural network model, a C4.5 model, a k-means model, or a combination of one or more of the foregoing. Other suitable types of machine or statistical learning models are also contemplated. It will also be appreciated that the machine-learned model 156 can use certain mathematical methods alone or in combination with one or more machine or statistical learning models to adjust the parameter trend line.

The water contaminant measurement system and methods described herein provide a number of advantages and benefits. For instance, the water contaminant measurement system and methods described herein provide a relatively low cost measurement system and techniques that allow for rapid, onsite concentration level measurements to be determined. Thus, reliance on costly conventional systems that require long measurement turnaround times is reduced. The water contaminant measurement system and methods described herein may be utilized for point of entry applications, point of use applications, in water treatment and processing facilities, in homes and buildings, and may be integrated or in line with filter devices. Further, the water contaminant measurement system and methods described herein may be utilized to detect any suitable preselected contaminant, such as e.g., lead, cadmium, chromium, as well as other contaminants. By changing the chemistry or treatment of the detecting agent, the concentration level of any suitable contaminant may be measured and presented to a user. Other benefits and advantages not specifically listed herein are possible.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A contaminant measurement system for measuring a concentration level of a preselected contaminant in a volume of water, the contaminant measurement system comprising:
   a housing defining a chamber configured for receipt of the volume of water;
   a detection agent disposed in a basket in the volume of water in the chamber;
   a sensing circuit having a first electrode and a second electrode both disposed in the basket at least partially in the volume of water in the chamber, the first electrode spaced at a distance from the second electrode; and
   a controller in electrical communication with the sensing circuit, the controller configured to:
   receive one or more electric signals from the sensing circuit, the one or more signals being captured as the detection agent selectively interacts with the preselected contaminant in the volume of water for a first time period;
   determine a parameter value indicative of the concentration level of the preselected contaminant in the volume of water based at least in part on the one or more electric signals;
   determine the concentration level of the preselected contaminant in the volume of water in the chamber based at least in part on the parameter value, and wherein in determining the concentration level of the preselected contaminant, the controller is further configured to:
   calculate a parameter difference value for the determined parameter value, wherein the parameter difference value for the determined parameter value is descriptive of a base reference parameter value subtracted from the determined parameter value; and
   correlate the calculated parameter difference value for the determined parameter value to the concentration level of the preselected contaminant in the volume of water in the chamber utilizing a trend line determined during a calibration specific to the contaminant measurement system; and
   output the concentration level of the preselected contaminant in the volume of water in the chamber.

2. The contaminant measurement system of claim 1, wherein the detection agent is a plurality of beads, wherein the plurality of beads is a plurality of sodium hydroxide treated polyacrylonitrile homopolymer beads.

3. The contaminant measurement system of claim 2, wherein the preselected contaminant is lead.

4. The contaminant measurement system of claim 1, further comprising: a display device communicatively coupled with the controller, and wherein the concentration level is output by the controller to the display device so that the determined concentration level is presented to a user.

5. The contaminant measurement system of claim 1, wherein the first electrode is formed of a first electrically conducting material and the second electrode is formed of a second electrically conducting material dissimilar to the first electrically conducting material.

6. The contaminant measurement system of claim 5, wherein the first electrically conducting material of the first electrode is copper and the second electrically conducting material of the second electrode is graphite.

7. The contaminant measurement system of claim 1, wherein the housing has an inlet port defining an inlet of the chamber and an outlet port defining an outlet of the chamber, and wherein the contaminant measurement system further comprises:
an inlet supply conduit providing fluid communication between a water source and the inlet of the chamber;
an inlet valve positioned along the inlet supply conduit and operable to selectively allow the volume of water to flow into the chamber; and
an outlet supply conduit in fluid communication with the outlet of the chamber, the outlet supply conduit operable to allow the volume of water to drain from the chamber.

8. The contaminant measurement system of claim 1, wherein the parameter value is indicative of at least one of a voltage between the first electrode and the second electrode, an electrolytic current flowing between the first electrode and the second electrode, a conductivity of the volume of the water within the chamber, and a resistivity of the volume of water within the chamber.

9. The contaminant measurement system of claim 1, wherein in performing the calibration, the controller is configured to:
ascertain the base reference parameter value indicative of the concentration level of the preselected contaminant in a volume of water having a first known concentration level of the preselected contaminant;
ascertain a plurality of reference parameter values each indicative of the concentration level of the preselected contaminant in respective reference volumes of water each having a known concentration level of the preselected contaminant;
calculate a parameter difference value for the ascertained base reference parameter value and each of the plurality of ascertained reference parameter values, wherein the parameter difference value for each of the plurality of ascertained reference parameter values is descriptive of the ascertained base reference parameter value subtracted from a given one of the ascertained reference parameter values, and wherein the parameter difference value for the base reference parameter value is zero; and
determine the trend line specifying the parameter difference value versus the concentration level based at least in part on the calculated parameter difference values.

10. The contaminant measurement system of claim 9, wherein the determined parameter value used to determine the concentration level of the preselected contaminant in the volume of water within the chamber is based on one or more final signals of the one or more signals received at an end time of the first time period.

11. The contaminant measurement system of claim 10, wherein the end time of the first time period is determined based on the determined parameter value reaching a steady state.

12. The contaminant measurement system of claim 1, wherein the controller is further configured to:
store a plurality of data points representative of the determined parameter values over the first time period;
generate a parameter trend line based at least in part on the stored plurality of data points; and
predict the parameter value based at least in part on the parameter trend line.

13. The contaminant measurement system of claim 12, wherein the parameter value used to determine the concentration level of the preselected contaminant in the volume of water within the chamber is based on the predicted parameter value.

14. The contaminant measurement system of claim 12, wherein the parameter value is indicative of at least one of a voltage between the first electrode and the second electrode, an electrolytic current flowing between the first electrode and the second electrode, a conductivity of the volume of the water within the chamber, and a resistivity of the volume of water within the chamber.

15. The contaminant measurement system of claim 12, wherein the parameter trend line is a decaying exponential function.

16. The contaminant measurement system of claim 1, wherein the controller is further configured to:
cause a voltage to be applied across the first electrode and the second electrode both at least partially disposed in the volume of water within the chamber.

17. The contaminant measurement system of claim 1, wherein the first electrode and the second electrode are connected to a top cap that is removably seated on the housing.

18. The contaminant measurement system of claim 17, wherein the basket is connected to the top cap, the basket defining a basket chamber in which the detection agent is disposed, the basket chamber being in flow communication with the chamber of the housing.

* * * * *